(12) United States Patent
Hsi et al.

(10) Patent No.: US 10,792,026 B2
(45) Date of Patent: Oct. 6, 2020

(54) FILM DEVICE AND METHOD OF USING THE SAME

(71) Applicant: The Research Foundation for The State University of New York, Albany, NY (US)

(72) Inventors: Hsingli Kai Hsi, Albany, NY (US); Mark Talamini, Albany, NY (US)

(73) Assignee: The Research Foundation for The State University of New York, Albany, NY (US)

(*) Notice: Subject to any disclaimer, the term of this patent is extended or adjusted under 35 U.S.C. 154(b) by 157 days.

(21) Appl. No.: 15/776,875

(22) PCT Filed: Dec. 2, 2016

(86) PCT No.: PCT/US2016/064622
§ 371 (c)(1),
(2) Date: May 17, 2018

(87) PCT Pub. No.: WO2017/096168
PCT Pub. Date: Jun. 8, 2017

(65) Prior Publication Data
US 2018/0333151 A1    Nov. 22, 2018

Related U.S. Application Data

(60) Provisional application No. 62/262,065, filed on Dec. 2, 2015.

(51) Int. Cl.
*A61B 17/02*    (2006.01)
*A61B 90/00*    (2016.01)
(Continued)

(52) U.S. Cl.
CPC ...... *A61B 17/0218* (2013.01); *A61B 17/0293* (2013.01); *A61B 90/04* (2016.02);
(Continued)

(58) Field of Classification Search
CPC .......... A61B 17/00234; A61B 17/0293; A61B 17/3211; A61B 17/3423;
(Continued)

(56) References Cited

U.S. PATENT DOCUMENTS

| 5,037,379 A | 8/1991 | Clayman et al. |
| 2013/0331802 A1 | 12/2013 | Collinge et al. |

(Continued)

FOREIGN PATENT DOCUMENTS

WO    WO 2015/164591 A1    10/2015

OTHER PUBLICATIONS

International Search Report dated Feb. 17, 2017 issued in PCT/US2016/064622.

*Primary Examiner* — Christine H Matthews
(74) *Attorney, Agent, or Firm* — Scully Scott Murphy and Presser (57) ABSTRACT

The present disclosure is directed to a surgical device and method of using the same. The surgical device includes a proximal ring, a distal ring, wherein the distal ring is operably connected to the proximal ring with a sleeve, the sleeve extending about a circumference of the proximal ring and a circumference of the distal ring, a film, a distal end of the film attached to a portion of the distal ring, wherein the film is configured to extend past the sleeve and past the distal ring, and wherein a proximal portion of the film comprises an opening and a channel and a draw string extending through the channel and exposed to an exterior of the device through the opening.

9 Claims, 4 Drawing Sheets

(51) Int. Cl.
    *A61B 90/40*           (2016.01)
    *A61B 17/34*           (2006.01)
    *A61B 17/00*           (2006.01)

(52) U.S. Cl.
    CPC .......... *A61B 90/40* (2016.02); *A61B 17/3423* (2013.01); *A61B 2017/00287* (2013.01); *A61B 2017/0225* (2013.01); *A61B 2090/0427* (2016.02)

(58) Field of Classification Search
    CPC ........... A61B 2017/00287; A61B 2017/00557; A61B 2017/320024; A61B 2017/3466; A61B 2017/0225; A61B 2090/0427; A61B 90/04; A61B 90/40
    See application file for complete search history.

(56) References Cited

U.S. PATENT DOCUMENTS

| | | |
|---|---|---|
| 2015/0201922 A1 | 7/2015 | Shibley et al. |
| 2016/0100857 A1* | 4/2016 | Wachli ............... A61B 17/3439 600/204 |

\* cited by examiner

# FILM DEVICE AND METHOD OF USING THE SAME

CROSS-REFERENCE TO RELATED APPLICATIONS

This application claims the benefit of U.S. Provisional Application No. 62/262,065 filed on Dec. 2, 2015, the entire contents of which is incorporated herein by reference.

BACKGROUND OF THE DISCLOSURE

Surgical devices that maintain an opening between a patient's internal cavity and the exterior environment merely create pressure about an incision to maintain the incision in an open configuration. In surgical methods where a patient's internal organs are removed from the patients' body for a period, the re-entry of those organs requires concentrated pressure on small portions of those organs by a surgeons hands or with instruments operated by the surgeon. Also, in these surgical methods the organs themselves can come into contact with foreign elements which may not be sterilized.

Therefore, what is desired is a device that can be used to maintain extracted elements in a substantially sterile environment and also aid in the re-entry of the extracted elements into the patient's internal cavity. Embodiments of the present disclosure provide devices and methods that address the above and other issues.

SUMMARY OF THE DISCLOSURE

The present disclosure is directed to a surgical device and method of using the same. The surgical device includes a proximal ring, a distal ring, wherein the distal ring is operably connected to the proximal ring with a sleeve, the sleeve extending about a circumference of the proximal ring and a circumference of the distal ring, a film, a distal end of the film attached to a portion of the distal ring, wherein the film is configured to extend past the sleeve and past the distal ring, and wherein a proximal portion of the film comprises an opening and a channel and a draw string extending through the channel and exposed to an exterior of the device through the opening.

BRIEF DESCRIPTION OF THE DRAWINGS

The present disclosure will be better understood by reference to the following drawings of which.

DETAILED DESCRIPTION OF THE DISCLOSURE

As used herein, the term "substantially", or "substantial", is equally applicable when used in a negative connotation to refer to the complete or near complete lack of an action, characteristic, property, state, structure, item, or result. For example, a surface that is "substantially" flat would either completely flat, or so nearly flat that the effect would be the same as if it were completely flat.

As used herein, the term "about" indicates that the value listed may be somewhat altered, as long as the alteration does not result in nonconformance of the process or structure to the illustrated embodiment. For example, for some elements the term "about" can refer to a variation of ±0.1%, for other elements, the term "about" can refer to a variation of ±1% or ±10%, or any point therein.

Figure 1:
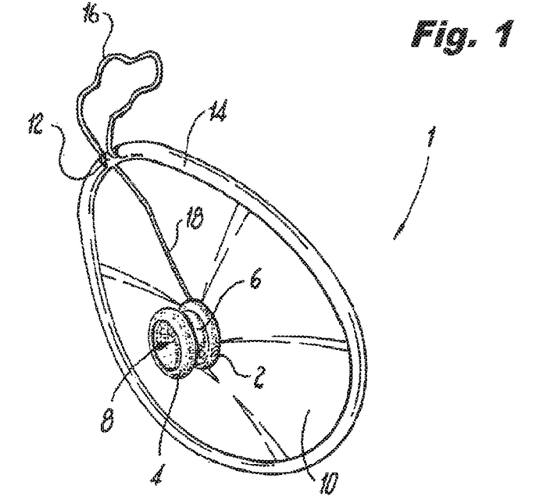
FIG. 1 is a perspective view of a first embodiment of a surgical device.

This disclosure includes a surgical device 1, as shown in FIG. 1. The surgical device 1 includes a proximal ring 2. Proximal ring 2 is shown in an expanded configuration in FIG. 1, but proximal ring 2 is deformable but will return to its expanded configuration once the deforming pressure is no longer exerted. Once deformed, proximal ring 2 can be manipulated to enter an opening in a patient that can be smaller than the diameter of the proximal ring 2. As used herein, the patient can be any suitable mammal, including but not limited to humans, canines felines, equines, bovines, various livestock including swine, sheep and poultry, and rodents.

Proximal ring 2 is formed of any suitable material that is flexible and can be deformed and then return to an expanded configuration, such as a suitable metal or combination of metals, a foam, including but not limited to a polyisoprene foam, a suitable plastic or elastomer including but not limited to silicone rubber, latex, polyethylene C-flex, polyurethane, polyisoprene, silicone, and other thermoplastic elastomers (TPE), and combinations thereof.

Surgical device 1 also includes a distal ring 4 that is formed of any material that is flexible and can be deformed and then return to an expanded configuration, such as a suitable metal or combination of metals, a foam, including but not limited to a polyisoprene foam, a suitable plastic or elastomer including but not limited to silicone rubber, latex, polyethylene C-flex, polyurethane, polyisoprene, silicone, and other thermoplastic elastomers (TPE), and combinations thereof.

Proximal ring 2 and distal ring 4 can be the same or different and are any suitable diameter, such as between about 2 cm and about 25 cm with all dimensions in between. In other embodiments, the diameter dimensions of proximal ring 2 and distal ring 4 can be modified by 100% or more.

The distal ring 4 is operably connected to the proximal ring 2 with a sleeve 6. Sleeve 6 is formed of any material that is flexible and can be deformed and then return to an expanded configuration, such as a suitable metal or combination of metals, a foam, including but not limited to a polyisoprene foam, a suitable plastic or elastomer including but not limited to silicone rubber, latex, polyethylene C-flex, polyurethane, polyisoprene, silicone, and other thermoplastic elastomers (TPE), and combinations thereof.

Sleeve 6 extends around the circumference of proximal ring 2 and around the circumference of distal ring 4, thereby operably connecting proximal ring 2 to distal ring 4. The sleeve 6, proximal ring 2 and distal ring 4 form a substantially cylindrical conduit 8, allowing for the passage of material and instruments therethrough.

The surgical device 1 also includes a film 10, the distal end of which is operably connected to the distal ring 4 through the conduit 8. Film 10 can be formed of any suitable material that is flexible, including plastic materials including but not limited to any suitable elastomer or thermoplastic, including but not limited to, a polyurethane, low density polyethylenes, high density polyethylenes, vinyl, polyvinyl chloride (PVC), polyethylene terephthalate (PET), polyethersulfone (PES), cyclo olefin copolymer (COC), polymethyl methacrylate or poly methyl 2-methylpropanoate (PMMA). In other embodiments film 10 can be any other suitable material that is substantially antimicrobial, substantially hydrophobic, substantially able to be sterilized and substantially able to prevent or reduce burns from the electrocautery or harmonic scalpel.

The film 10 can be of any suitable diameter depending on the desired results. For example, the film 10 can have a diameter of between about 4 cm and about 200 cm with all dimensions in between. In other embodiments, the diameter dimensions of proximal ring 2 and distal ring 4 can be modified by 100% or more. Film 10 can also be in other suitable shapes of similar sizes, such as a square shape, a pentagon shape, etc.

Thickness of the film 10 can be modified on desired results and can range from about 0.01 mm to about 10 mm, including all thicknesses between. The thickness of film 10 can be modified such that film 10 is above a burst pressure upon delivery of a pressure as described below. For example, the film 10 can be configured to withstand burst pressures up to and including about 25 mm Hg. In other embodiments, film 10 can be configured to withstand burst pressures more than 25 mm Hg.

The film 10 also includes a proximal portion of the film, which comprises an opening 12 and a channel 14. The channel 14 extends about the majority of the circumference of the proximal portion of the film 10 and is configured to maintain and allow a drawstring 16 to pass therethrough. Drawstring 16 is accessible from the exterior of surgical device 1 through the opening 12. Drawstring can be composed of any suitable material having a sufficient tensile strength, such as string, twine, cable, rope and the like.

Drawstring 16 is configured such that upon pulling of the drawstring 16 through opening 12, the circumference of the proximal portion of the film is reduced until the majority of the proximal portion of the film is in contact with itself.

Film 10 also has a seam 18, which can be either sealed by any suitable process, or left open.

Figure 2:
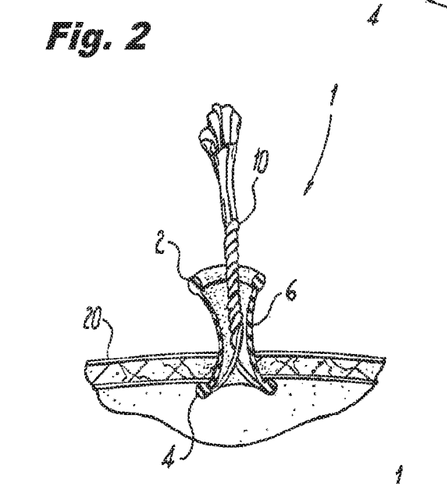
FIG. 2 is a perspective view of the surgical device during use.
Figure 3:
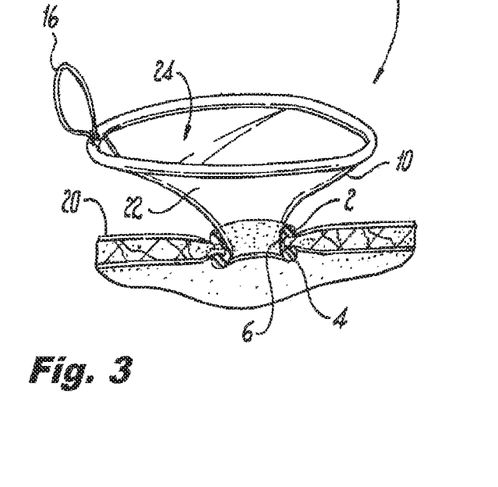
FIG. 3 is a perspective view of the surgical device during use.

FIG. 2 illustrates a side view of surgical device 1 as it is being installed. During use, an incision is initially made into a portion of a patient 20, such as in making an incision to access the abdominal cavity of the patient. Then, the distal ring 4 is deformed, inserted through the formed incision and then allowed to return to its expanded configuration, as shown in FIG. 2. The proximal ring 2 is then rolled over sleeve 6 to adjust for the thickness of the cavity wall of the portion of the patient 20, if needed. Once the proximal ring 2 contacts the portion of the patient 20, the film 10 can be expanded to expose an exterior surface 22 of the film 10 and an interior surface 24 of the film 10, as shown in FIG. 3.

The interior surface 24 of film 10 can be substantially sterile so that contact with the interior surface 24 by a portion of the patient does not transfer a substantial amount of microorganisms. As used herein, the term "sterile" means freedom, to a specified degree, from microorganisms. In one example, the degree of freedom from microorganisms is measured to a concentration of about $1\times10^6$ colony forming units (CFU) or less.

Figure 4:
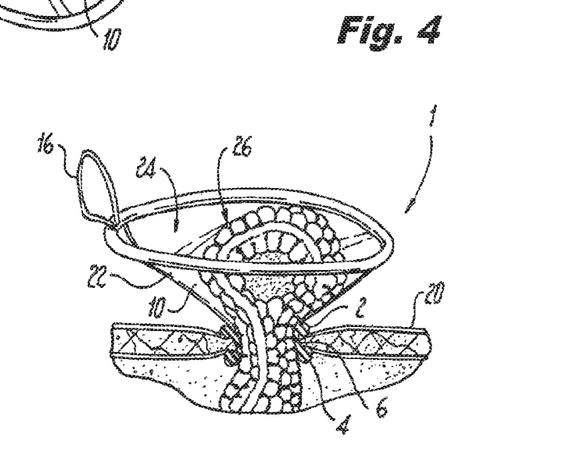
FIG. 4 is a perspective view of the surgical device during use.

Then, as shown in FIG. 4, one or more portions of the patients' intestines or organs 26 can be removed from the interior of the patient, past the distal ring 4, the sleeve 6, the proximal ring 2 and into contact with the interior surface 24. The surgeon can then perform the proper procedure while the organs 26 are removed from the interior of the patient and in contact with the interior surface 24.

Figure 5:
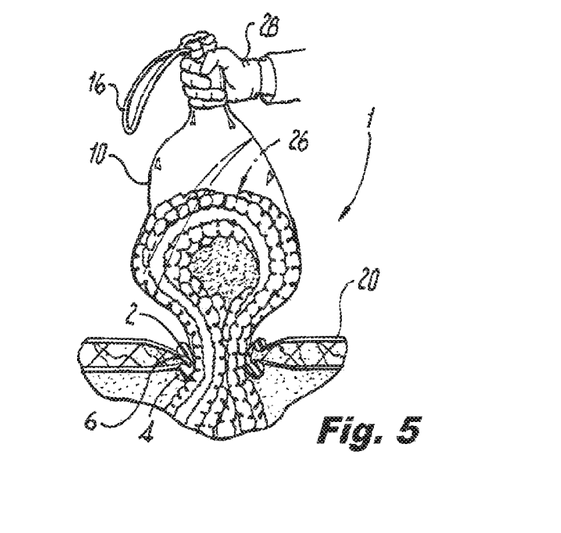
FIG. 5 is a perspective view of the surgical device during use.

Once the procedure is completed, the patients' organs 26 are reintroduced into the interior of the patient with aid of the surgical device 1. As shown in FIG. 5, the drawstring 16 is pulled upon such that the circumference of the proximal portion of the film 10 is reduced and the majority of the proximal portion of the film 10 is in contact with itself. The film 10 can also be twisted during and after the pulling of drawstring to further reduce the volume within film 10 and to aid in a seal of the proximal portion of the film.

Figure 6:
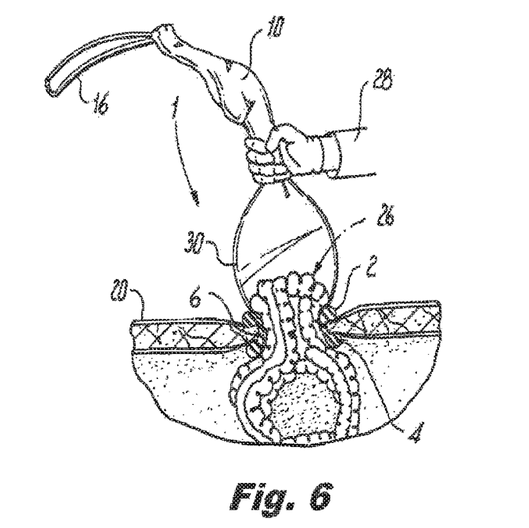
FIG. 6 is a perspective view of the surgical device during use.

A surgeon or other user can use their hand 28, or in other embodiments both hands or one or more devices that can maintain the proximal portion of film 10 in a close relationship, to hold the proximal portion of the film 10 together. Once the proximal portion of film 10 is substantially sealed, the user's hand then slides away from the proximal portion of film 10 towards proximal ring 2, as shown in FIG. 6. This motion reduces the circumference of the film 10 from the proximal portion of the film towards the proximal ring 2. As the user's hand 28 slides, it maintains the substantial seal, forming a pocket of gas 30, such as air, under a pressure. The pressure in the pocket of gas can also be formed or maintained by at least one of a supplied, pressurized gas, such as air or carbon dioxide or other suitable gases, and a saline solution. The pressurized gas and the saline solution can enter pocket 30 through a valve (not shown) in film 10.

This pressure aids in causing the organs 26 to be reintroduced into the patient.

During the procedure film 10 can be expanded again to form a larger pocket of air 30, if needed.

Figure 7:
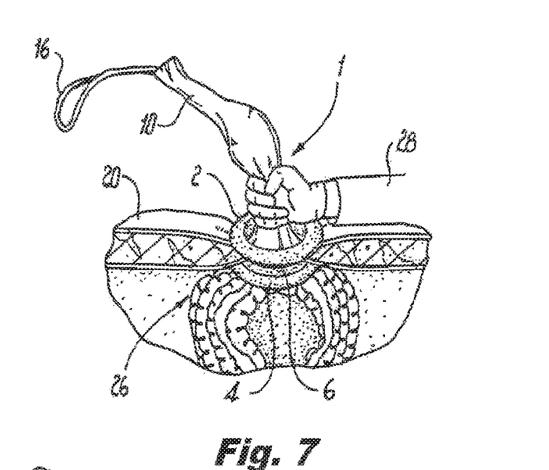
FIG. 7 is a perspective view of the surgical device during use.

As the user's hand 28 continues to slide towards proximal ring 2 the pressure in pocket of air 30 causes the organs 26 to reenter the patient, as shown in FIG. 7. The user may also provide pressure to organs 26 through the film 10 with their hand 28 or another device to aid in reentry of the organs 26.

Figure 8:
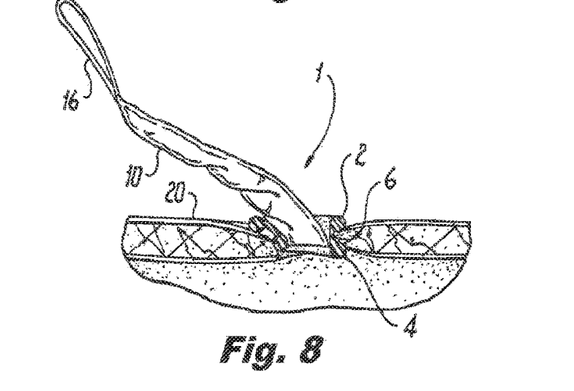
FIG. 8 is a perspective view of the surgical device during use.

Once the organs 26 have reentered the patient, the surgical device 1 can be removed, as shown in FIG. 8. A user can grasp film 10 or drawstring 16 and can pull away from the portion of the patient, causing distal ring 4 to deform and exit the incision. In other embodiments, distal ring 4 can be manually deformed prior to removal and pulling of the film 10 to aid in distal ring 4's exit from the incision.

Figure 9:
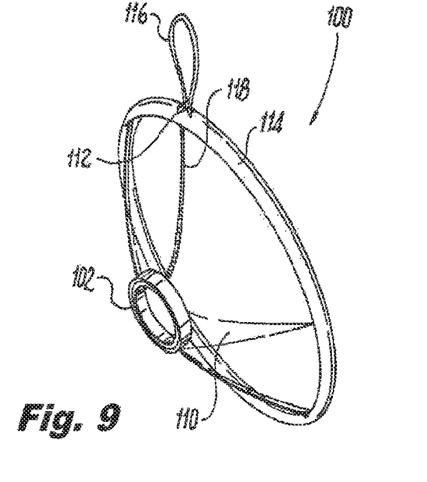
FIG. 9 is a perspective view of a second embodiment of a surgical device.

A second embodiment of a surgical device 100 is shown in FIG. 9 and now described. Surgical device 100 includes a proximal ring 102. Proximal ring 102 is shown in an expanded configuration in FIG. 9, but proximal ring 102 is deformable but will return to its expanded configuration once the deforming pressure is no longer exerted.

Proximal ring 102 is formed of any suitable material that is flexible and can be deformed and then return to an expanded configuration, such as a suitable metal or combination of metals, a foam, including but not limited to a polyisoprene foam, a suitable plastic or elastomer including but not limited to silicone rubber, latex, polyethylene C-flex, polyurethane, polyisoprene, silicone, and other thermoplastic elastomers (TPE), and combinations thereof.

The surgical device 100 also includes a film 110, the distal end of which is operably connected to the proximal ring 102. Film 110 can be the same or similar film as film 10 discussed above.

Film 110 also includes a proximal portion of the film, which comprises an opening 112 and a channel 114. The channel 114 extends about the majority of the circumference of the proximal portion of the film 110 and is configured to maintain and allow a drawstring 116 to pass therethrough. Drawstring 116 is accessible from the exterior of surgical device 100 through the opening 112. Drawstring can be composed of any suitable material having a sufficient tensile strength, such as string, twine, cable, rope and the like.

Drawstring 116 is configured such that upon pulling of the drawstring 116 through opening 112, the circumference of the proximal portion of the film is reduced until the majority of the proximal portion of the film is in contact with itself. Film 110 also has a seam 118, which can be either sealed by any suitable process, or left open.

Figure 10:
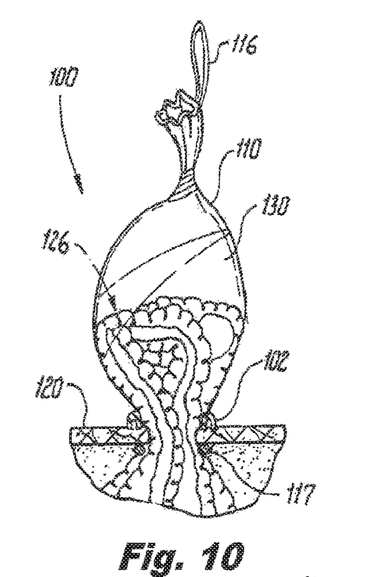
FIG. 10 is a perspective view of the surgical device during use.
Figure 11:
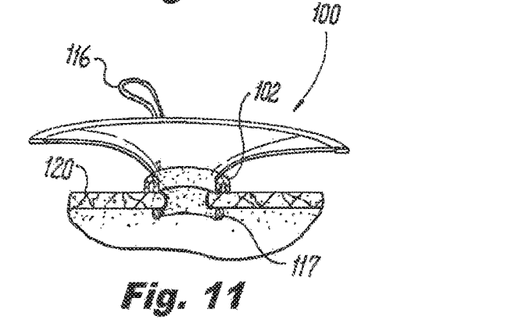
FIG. 11 is a perspective view of the surgical device during use.

Proximal ring 102 is configured to attach to an exterior portion of a known wound protector, as shown in FIG. 10. Known wound protector 117 is inserted in an incision of a patient to maintain the incision in the portion of the patient 120 in an open configuration. Once proximal ring 102 is attached to the wound protector 117, surgical device 100 is operated in substantially the same way as surgical device 1 discussed above, including the formation of a gas pocket 130 as shown in FIG. 11.

To remove surgical device 100 after operation, the proximal ring 102 is detached from wound protector 117.

Figure 12:
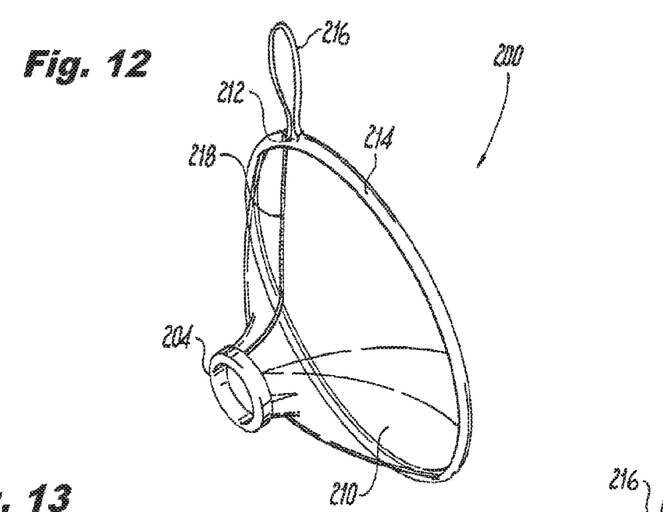
FIG. 12 is a perspective view of a third embodiment of a surgical device.

A third embodiment of a surgical device 200 is shown in FIG. 12 and now described. Surgical device 200 includes a distal ring 204. Distal ring 204 is shown in an expanded configuration in FIG. 12, but distal ring 204 is deformable but will return to its expanded configuration once the deforming pressure is no longer exerted.

Distal ring 204 is formed of any suitable material that is flexible and can be deformed and then return to an expanded configuration, such as a suitable metal or combination of metals, a foam, including but not limited to a polyisoprene foam, a suitable plastic or elastomer including but not limited to silicone rubber, latex, polyethylene C-flex, polyurethane, polyisoprene, silicone, and other thermoplastic elastomers (TPE), and combinations thereof.

The surgical device 200 also includes a film 210, the distal end of which is operably connected to the distal ring 204. Film 210 can be the same or similar film as film 10 discussed above.

Film 210 also includes a proximal portion of the film, which comprises an opening 212 and a channel 214. The channel 214 extends about the majority of the circumference of the proximal portion of the film 210 and is configured to maintain and allow a drawstring 216 to pass therethrough. Drawstring 216 is accessible from the exterior of surgical device 200 through the opening 212. Drawstring can be composed of any suitable material having a sufficient tensile strength, such as string, twine, cable, rope and the like.

Drawstring 216 is configured such that upon pulling of the drawstring 216 through opening 212, the circumference of the proximal portion of the film is reduced until the majority of the proximal portion of the film is in contact with itself. Film 210 also has a seam 218, which can be either sealed by any suitable process, or left open.

Figure 13:
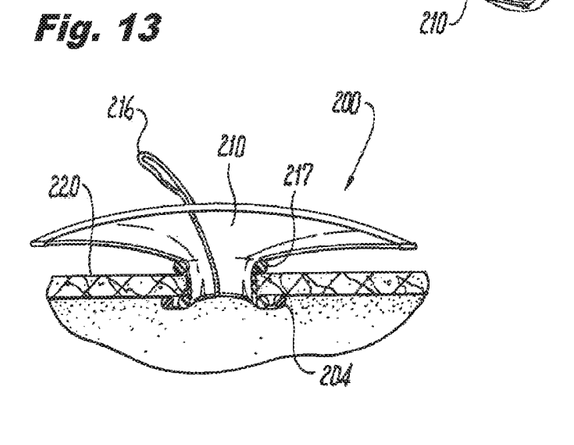
FIG. 13 is a perspective view of the surgical device during use.

Distal ring 204 is configured deform to fit within an opening of a known would protector, as shown in FIG. 13. Wound protector 217 is inserted in an incision of a patient to maintain the incision in the portion of the patient 220 in an open configuration. Once distal ring 204 is deformed and passes through the opening in wound protector 217, distal ring 204 is allowed to return to its expanded configuration, as shown in FIGS. 12 and 13.

Figure 14:
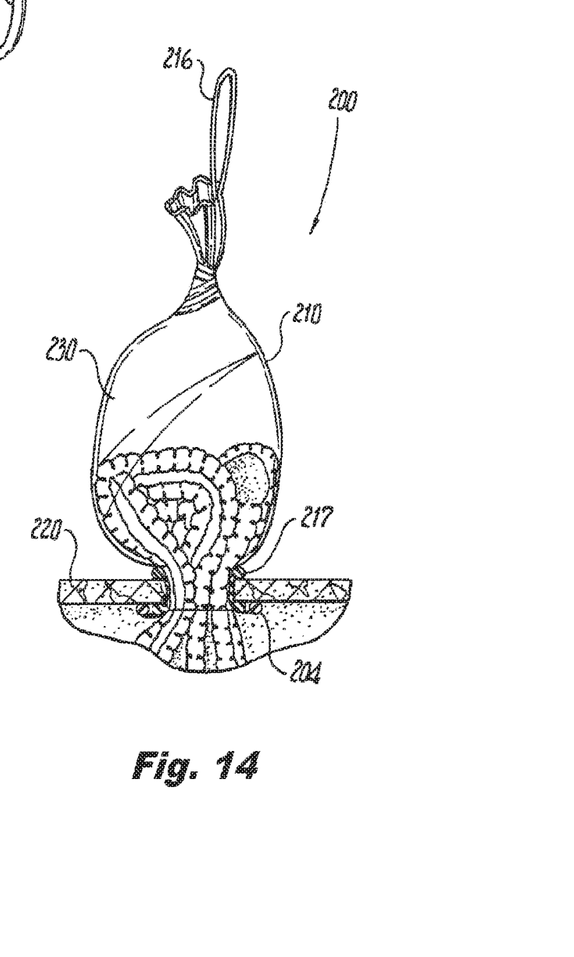
FIG. 14 is a perspective view of the surgical device during use.

The circumference of distal ring 204 is configured to be larger than the circumference of the internal portion of wound protector 217 such that distal ring 204 also contacts the portion of the patient 220 upon installation, as shown in FIG. 13. Once distal ring 204 is placed, the surgical device 200 is operated in substantially the same way as surgical device 1 discussed above, including the formation of a gas pocket 230 as shown in FIG. 14.

To remove surgical device 200, a user can grasp film 210 or drawstring 216 and can pull away from the portion of the patient 220, causing distal ring 204 to deform and exit the incision past the wound protector 217. In other embodiments, distal ring 204 can be manually deformed prior to removal and pulling of the film 210 to aid in distal ring 204's exit from the wound protector 217.

Figure 15:
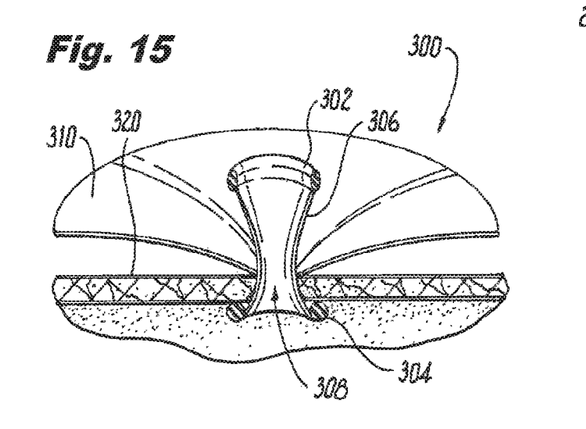
FIG. 15 is a side view of a fourth embodiment of a surgical device.

A fourth embodiment of a surgical device 300 is shown in FIG. 15 and now described. FIG. 15 illustrates a side view of surgical device 300 after it is installed.

Surgical device 300 includes a proximal ring 302. Proximal ring 302 is formed of any suitable material that is flexible and can be deformed and then return to an expanded configuration. Proximal ring 302 can be the same or similar as proximal ring 2 discussed above.

Surgical device 300 includes a distal ring 304. Distal ring 304 is shown in an expanded configuration in FIG. 15, but distal ring 304 is deformable and can return to the expanded configuration once the deforming pressure is no longer exerted. Distal ring 304 can be the same or similar as distal ring 4 discussed above.

The surgical device 300 also includes a film 310, the distal end of which is operably connected to the distal ring 304. Film 310 can be the same or similar film as film 10 discussed above. In this embodiment film 310 is operably connected to the distal ring 304 without passing through the substantially cylindrical conduit 208.

Although not shown in this figure the film 310 can include an opening, a channel and a drawstring as discussed in reference to FIGS. 1-8 above.

The distal ring 304 is operably connected to the proximal ring 302 with a sleeve 306. Sleeve 306 can be the same or similar to sleeve 6 discussed above.

Sleeve 306 extends around the circumference of proximal ring 302 and around the circumference of distal ring 304, thereby operably connecting proximal ring 302 to distal ring 304. The sleeve 306, proximal ring 302 and distal ring 304 form a substantially cylindrical conduit 308, allowing for the passage of material and instruments therethrough.

The proximal ring 302 is configured to roll over sleeve 306 to adjust for the thickness of the cavity wall of a portion of the patient 320. In this embodiment film 310 is operably connected to the distal ring 304 without passing through the substantially cylindrical conduit 308. In this embodiment, when sleeve 302 is rolled, the sleeve 302 contacts film 310 instead of contacting a portion of a patient 320 (as shown in FIG. 3 above), so that film 310 remains between both sleeve 306 and proximal ring 302 and the portion of the patient 320 during installation, operation and removal.

A fifth embodiment of a surgical device 400 is shown in FIGS. 16-19. Although surgical device 400 will be discussed below, it is similar to a combination of both surgical device 100 and surgical device 200.

Figures 16, 17, 18, 19:
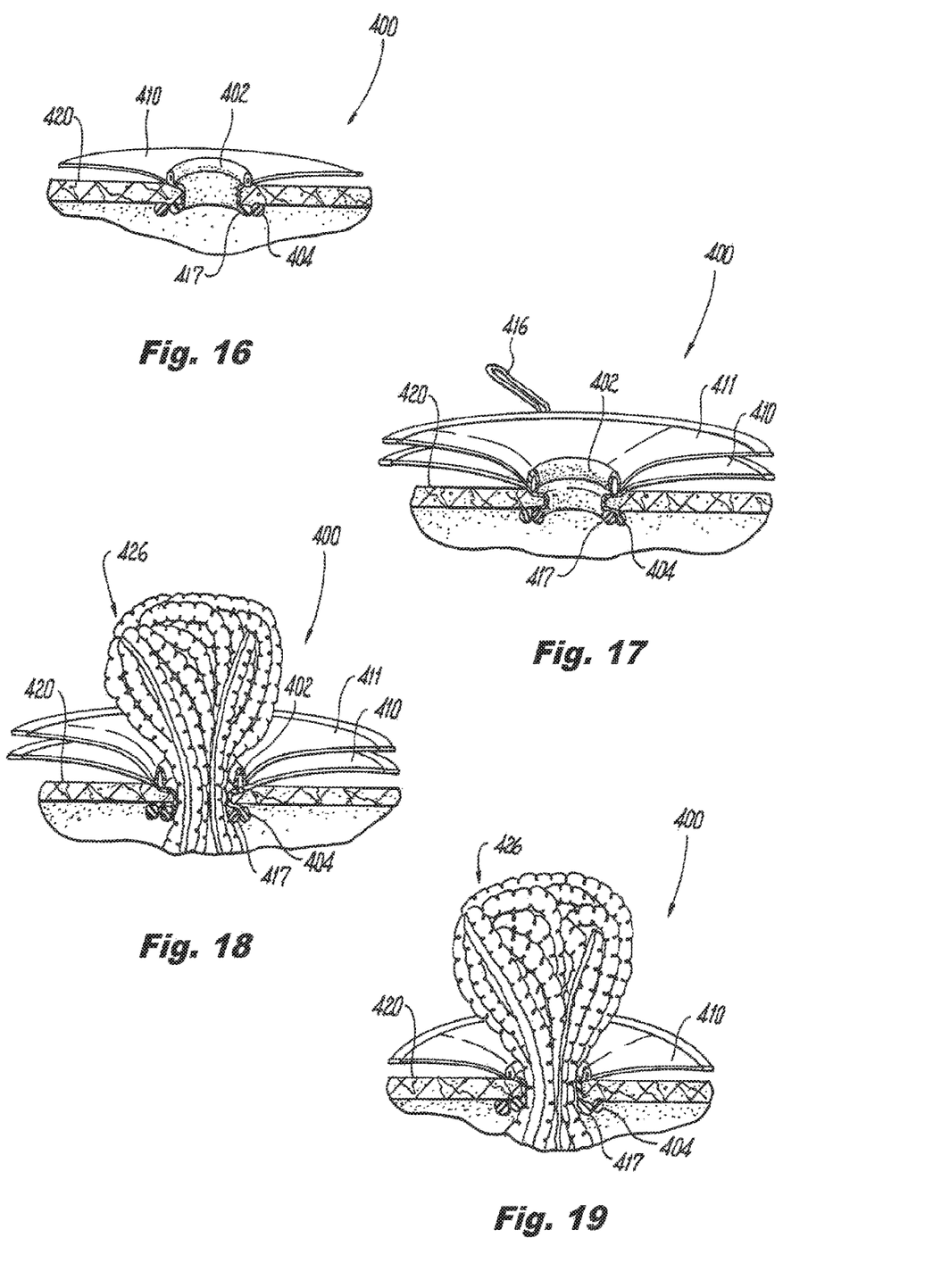
FIG. 16 is a side view of a fifth embodiment of a surgical device during use.
FIG. 17 is a side view of the surgical device during use.
FIG. 18 is a side view of the surgical device during use.
FIG. 19 is a side view of the surgical device during use.

In FIG. 16, a side view of surgical device 400 is shown after being inserted through an incision of a portion of a patient 420. Surgical device 400 includes a distal ring 404. Distal ring 404 is shown in an expanded configuration and is the same or similar to distal ring 204 discussed above.

The surgical device 400 also includes a first film 410, the distal end of which is operably connected to the distal ring 404. First film 410 can be the same or similar to film 10 discussed above.

Although not shown in this figure the first film 410 can include an opening, a channel and a drawstring as discussed in reference to FIGS. 1-8 above.

Distal ring 404 is configured deform and fit between the portion of the patient 420 and the exterior surface of a known would protector.

Once distal ring 404 is deformed and passes through the opening in the portion of the patient 420 and is allowed to return to its expanded configuration, a wound protector 417 is also placed in the opening in the portion of the patient 420. Wound protector 417 is inserted to maintain the incision in the portion of the patient 420 in an open configuration.

The circumference of distal ring 404 is configured to be larger than the circumference of the internal portion of wound protector 417 such that distal ring 404 contacts the portion of the patient 420 upon installation and the wound protector 417 contacts the distal ring 404 or the first film 410, as shown in FIG. 16.

After wound protector 417 and distal ring 404 are placed, a second film 411, the distal end of which is operably connected to a proximal ring 402 is introduced as shown in FIG. 17. This proximal ring 402 is the same or similar to proximal ring 102 as discussed above. Also, this second film 411 can be the same or similar to film 10 discussed above.

In FIG. 17 proximal ring 402 is shown in an expanded state, but proximal ring 401 is deformable.

Although not shown in this figure the second film 411 can include an opening and a channel as discussed in reference to FIGS. 1-8 above. As shown in FIG. 17, second film 411 includes a drawstring 416, which is the same or similar to the drawstring 116 discussed above.

Proximal ring 402 is configured to attach to an exterior portion of a known wound protector 417. Once proximal ring 402 is attached to the wound protector 417, surgical device 400 is operated in substantially the same way as surgical device 1 discussed above, including the formation of a gas pocket as shown in FIG. 11.

One example of this operation is shown in FIG. 18, which illustrates one or more portions of the patients' intestines or organs 426 removed from the interior of the patient. The intestines or organs 426 pass distal ring 404, wound protector 417, proximal ring 402, as well as first film 410 and second film 411.

Optionally, while the one or more portions of the patients' intestines or organs 426 removed from the interior of the patient, the first film 411, including the proximal ring 402 can be removed, as shown in FIG. 19.

The described embodiments and examples of the present disclosure are intended to be illustrative rather than restrictive, and are not intended to represent every embodiment or example of the present disclosure. While the fundamental novel features of the disclosure as applied to various specific embodiments thereof have been shown, described and pointed out, it will also be understood that various omissions, substitutions and changes in the form and details of the devices illustrated and in their operation, may be made by those skilled in the art without departing from the spirit of the disclosure. For example, it is expressly intended that all combinations of those elements and/or method steps which perform substantially the same function in substantially the same way to achieve the same results are within the scope of the disclosure. Moreover, it should be recognized that structures and/or elements and/or method steps shown and/or described in connection with any disclosed form or embodiment of the disclosure may be incorporated in any other disclosed or described or suggested form or embodiment as a general matter of design choice. Further, various modifications and variations can be made without departing from the spirit or scope of the disclosure as set forth in the following claims both literally and in equivalents recognized in law.

The invention claimed is:

1. A surgical device comprising:
   a proximal ring;
   a distal ring, wherein the distal ring is operably connected to the proximal ring with a sleeve, the sleeve extending about a circumference of the proximal ring and a circumference of the distal ring;
   a film, a distal end of the film attached to a portion of the distal ring, wherein the film is configured to extend past the sleeve and past the distal ring, and wherein a proximal portion of the film comprises an opening and a channel; and
   a draw string extending through the channel and exposed to an exterior of the device through the opening.

2. The surgical device of claim 1, wherein the film comprises an interior surface and an exterior surface, and wherein the interior surface is substantially sterile.

3. The surgical device of claim 1 wherein the film is attached to a portion of the distal ring by being operably connected to the distal ring through the sleeve.

4. A method of using a surgical device, the method comprising the steps of:
   deforming a distal ring of the surgical device, the surgical device comprising a proximal ring, the distal ring, wherein the distal ring is operably connected to the proximal ring with a sleeve, the sleeve extending about a circumference of the proximal ring and a circumference of the distal ring, a film, a distal end of the film attached to a portion of the distal ring, wherein the film is configured to extend past the sleeve and past the distal ring, and wherein a proximal portion of the film comprises an opening and a channel and a draw string extending through the channel and exposed to an exterior of the device through the opening;
   inserting the distal ring through an incision in a patient such that the distal ring expands to an expanded configuration in a cavity of the patient;
   expanding the film to expose an interior surface of the film;
   removing one or more organs or portions of organs from the cavity of the patient;

pulling the drawstring to reduce the circumference of a proximal portion of the film and form a gas pocket; and reducing the circumference of the film from the proximal portion of the film towards the proximal ring, wherein the gas pocket is maintained and wherein the film and the gas pocket are configured to apply pressure to the organs or portions of organs.

5. The method of claim 4, further comprising the step of rolling the proximal ring over the sleeve after inserting the distal ring.

6. The method of claim 4, further comprising twisting the film prior to reducing the circumference of the film.

7. The method of claim 4, further comprising twisting the film during reduction of the circumference of the film.

8. The method of claim 4, wherein the step of forming the gas pocket further comprises providing at least one of a supplied, pressurized gas and a saline solution.

9. The method of claim 4 wherein the film is expanded outside the incision and not in the cavity of the patient.

\* \* \* \* \*